United States Patent [19]

Chodorow

[11] Patent Number: 5,086,792

[45] Date of Patent: * Feb. 11, 1992

[54] DENTAL FLOSS LOOP DEVICES, AND METHODS OF MANUFACTURE AND PACKAGING SAME

[75] Inventor: Ingram S. Chodorow, Upper Saddle River, N.J.

[73] Assignee: Placontrol Corp., Montvale, N.J.

[*] Notice: The portion of the term of this patent subsequent to Feb. 28, 2006 has been disclaimed.

[21] Appl. No.: 533,937

[22] Filed: Jun. 4, 1990

Related U.S. Application Data

[63] Continuation of Ser. No. 312,341, Feb. 16, 1991, abandoned, which is a continuation of Ser. No. 820,100, Jan. 21, 1986, abandoned.

[51] Int. Cl.⁵ ............................................. A61C 15/00
[52] U.S. Cl. .................................................... 132/323
[58] Field of Search ........................ 132/321, 323, 329

[56] References Cited

U.S. PATENT DOCUMENTS

| | | | |
|---|---|---|---|
| 1,559,320 | 10/1925 | Hirsh | 132/323 |
| 2,180,522 | 11/1939 | Henne | 132/323 |
| 2,981,264 | 4/1961 | DeFelice | 132/323 |
| 3,802,445 | 4/1974 | Wesley | 132/321 |
| 4,016,892 | 4/1977 | Chodorow | 132/323 |
| 4,034,770 | 7/1977 | Trecker | 132/90 |
| 4,315,516 | 2/1982 | Zappel | 132/90 |
| 4,550,741 | 11/1985 | Krag | 132/93 |
| 4,807,752 | 2/1989 | Chodorow | 132/323 |

FOREIGN PATENT DOCUMENTS

| | | | |
|---|---|---|---|
| 3226129 | 1/1984 | Fed. Rep. of Germany | 132/323 |
| 8100959 | 4/1981 | PCT Int'l Appl. | 132/329 |

Primary Examiner—Cary E. O'Connor
Attorney, Agent, or Firm—Rosen, Dainow & Jacobs

[57] ABSTRACT

Dental floss loop devices are formed by a pair of parallel floss strands extending between and having their ends secured to a pair of spaced apart gripping elements. These devices are made by feeding a pair of continuous strands of floss from a source, molding onto these strands gripping elements at successively large and small intervals along the length of the strands, and cutting the strands at the small intervals. In a variation single gripping elements are molded onto continuous parallel strands at equal intervals afterwhich each single element is divided into separate halves, with the spaced apart halves being the pair of gripping elements for each device. The invention also includes dispenser packages for these devices.

10 Claims, 10 Drawing Sheets

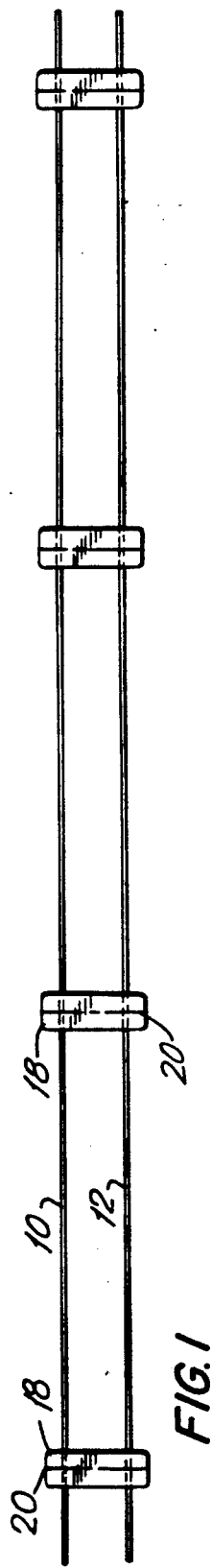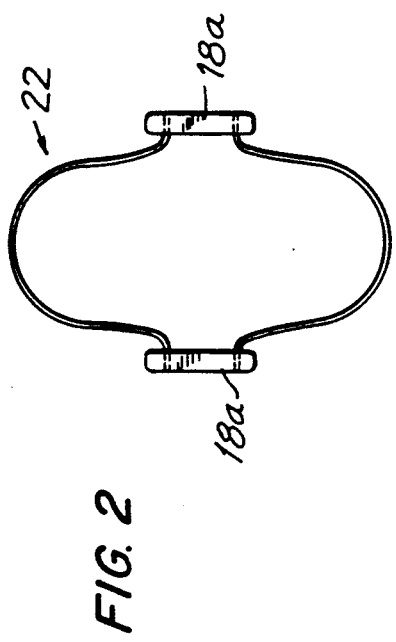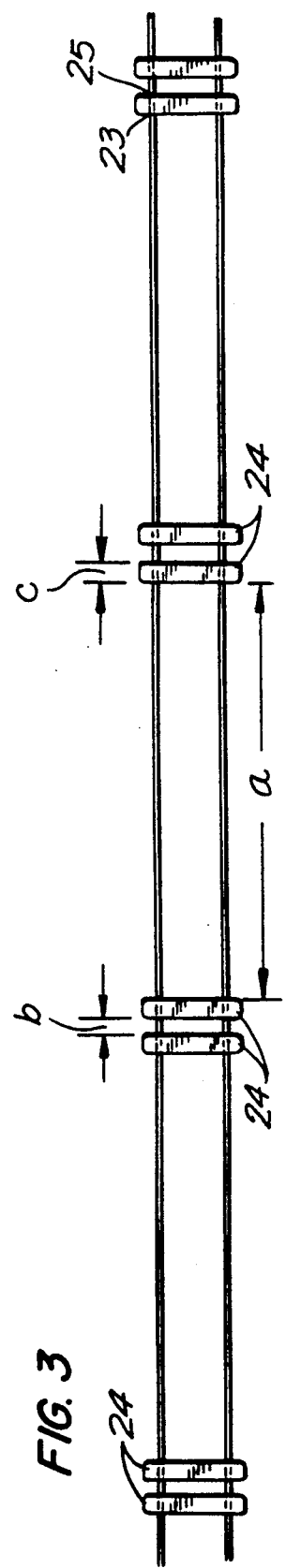

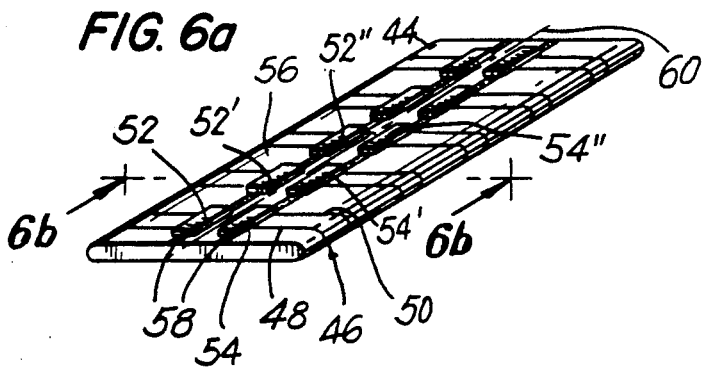
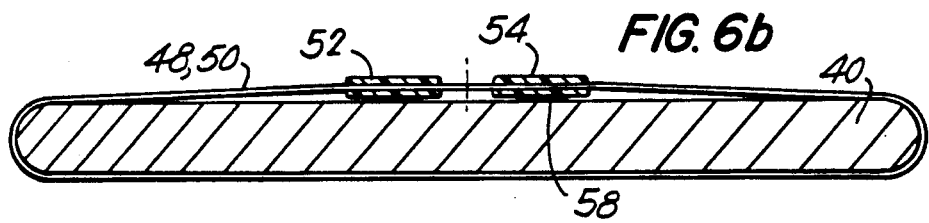
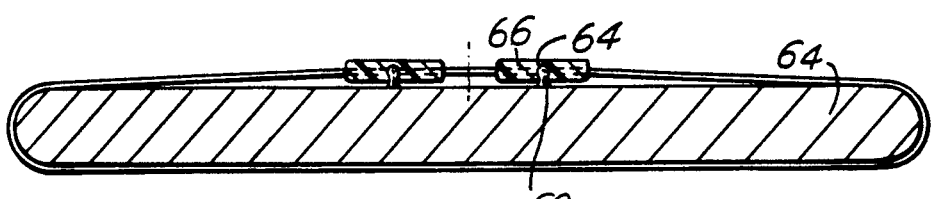
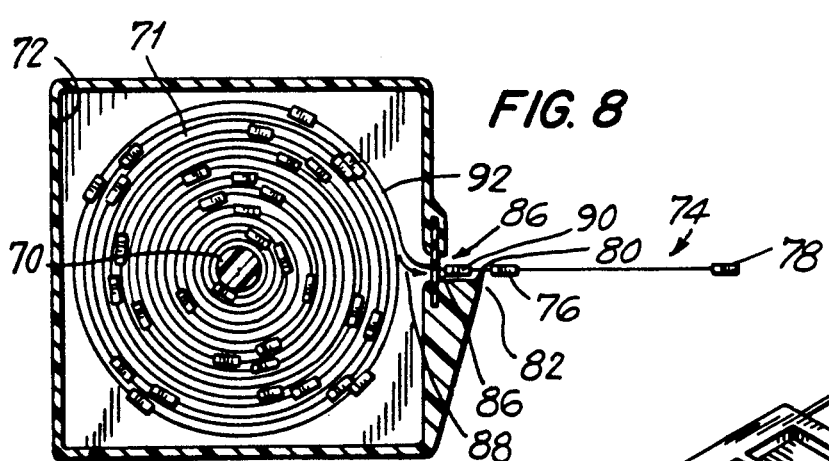
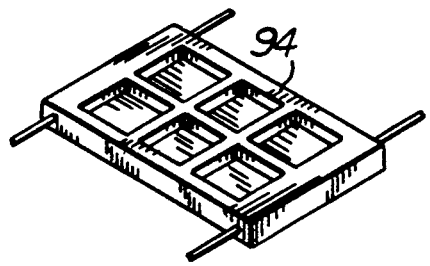
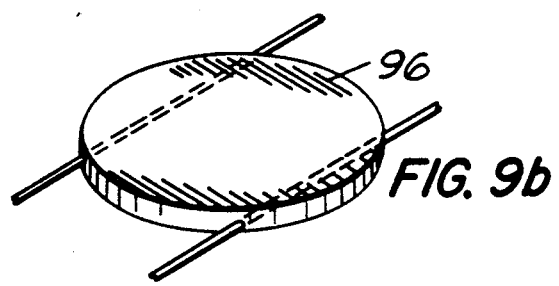

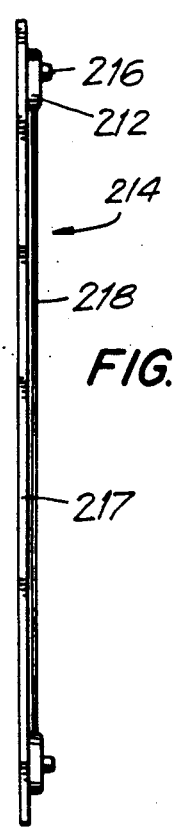
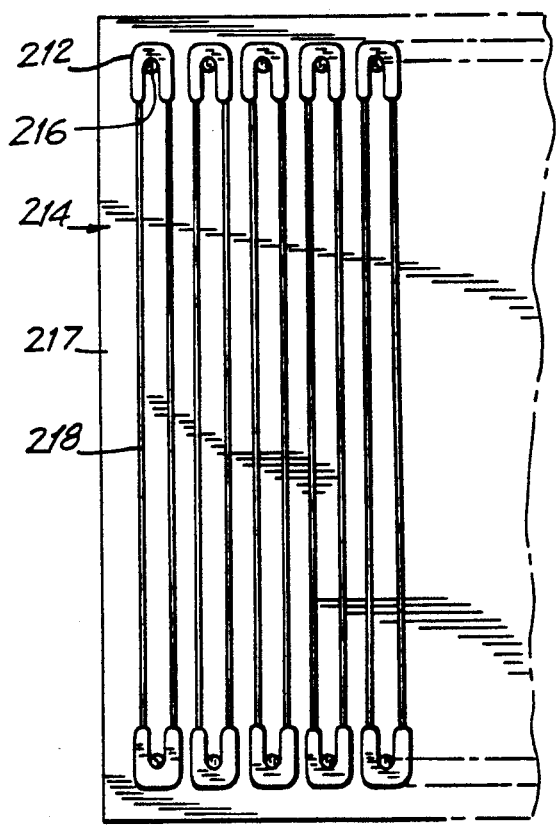
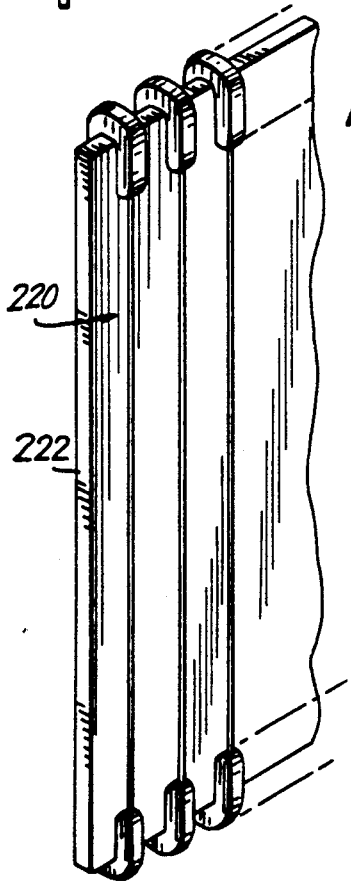
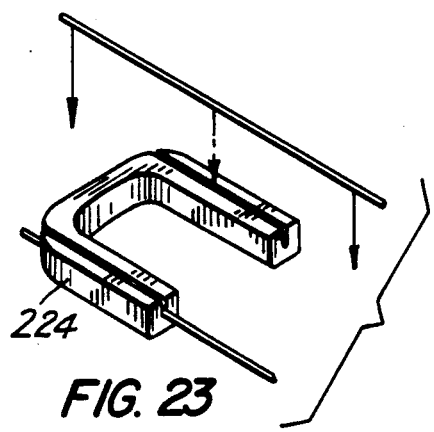
FIG. 21a
FIG. 21b
FIG. 22
FIG. 23

5,086,792

DENTAL FLOSS LOOP DEVICES, AND METHODS OF MANUFACTURE AND PACKAGING SAME

This application is a continuation of application Ser. No. 312,341 filed Feb. 16, 1989, now abandoned, which is a continuation of Ser. No. 820,100, now abandoned.

BACKGROUND OF THE INVENTION

This invention is in the field of dental floss devices formed into closed loops for manipulation by a person's fingers between adjacent teeth in a person's mouth and a method of manufacturing such loops and a method and apparatus for packaging and dispensing such loops. In dental health literature it has been well established that regular flossing between the teeth at least once a day is extremely useful in reducing and minimizing the amount of plaque buildup on tooth surfaces and particularly the crevice surfaces where adjacent teeth are close together and difficult if not impossible to reach and clean with a toothbrush. Typically floss has been used by uncoiling and cutting a strand of floss about eighteen inches long from a spool, wrapping ends of the strand about fingers on a person's two hands, and manipulating the strand between selected teeth in the mouth. This traditional technique consumes a substantial quantity of floss every time one engages in the flossing activity and requires considerable dexterity and/or endurance on the part of user's fingers which often experience pain since the floss is tightly wrapped around them can cut the skin or cause circulation to be temporarily cut off.

Various floss devices have been developed in attempts to reduce the difficulty of this oral health procedure. One of these approaches has been the development of dental floss holders such as those illustrated in U.S. Design Pat. Nos. D 227,896 which illustrates a V-shaped floss holder, and D 244,609 which illustrates an S-shaped floss holder, the latter having two segments of exposed floss as contrasted with a single segment in the former design. A later development and variation in this field of dental floss holders or devices is illustrated in U.S. Pat. No. 4,016,892 wherein a segment of floss has individual gripping elements at each end which can be held very easily and allow for similar ease of manipulation in the person's mouth without requiring the wrapping of floss around the finger. This new device uses about five inches of floss instead of eighteen to twenty-four and eliminates the inconvenience and/or discomfort of wrapping the floss around one's fingers. A still further variation in the field of floss devices is the formation of floss into a closed loop with two gripping elements secured on the circumference of the loop at two spaced apart locations. In use, a portion of the loop in between the gripping elements is maneuvered into the space between two adjacent teeth while the elements are held by pairs of fingers of the two hands respectfully as generally discussed in U.S. Pat. Nos. 4,315,516 and 4,315,517.

The purpose of the present invention is to provide an improved floss loop device along with an improved method of making such devices, and to provide simultaneous methods and apparatus for packaging these devices in practical dispenser containers. An object of the invention herein is to provide a very efficient, economic and high-speed technique and design for manufacturing the new devices and optionally for automatically and simultaneously packaging such devices into dispenser containers. A further object is to provide such dental floss loops with a structural design that constitutes an improvement over the various known prior art dental floss holder devices.

The invention possesses other objects and features of advantage, some of which will be apparent from the following description and the drawings. It is to be understood, however, that the invention is not limited to the embodiments illustrated and described since it may be embodied in various forms within the scope of the appended claims.

SUMMARY OF THE INVENTION

The invention herein provides improved floss loop devices along with an improved method of making these devices and also provides totally new dispenser packaging along with a method of forming such dispenser packages. In the method of manufacturing, a pair of continuous floss strands are disposed parallel and close together lengthwise along the axes of the strands. Separate gripping means are secured onto the parallel strands at predetermined intervals, these elements comprising a pair of gripping elements for each floss loop, the elements being either molded or otherwise adhered onto the strands. In one embodiment a single element is formed at predetermined intervals, and that element is subsequently divided into two parts with one part being one member of a pair of gripping elements of one floss loop unit and the other part being one member of the pair of gripping elements of the adjacent floss loop unit. In this manufacturing process the pair of continuous floss strands are directed to be in close parallel relationship from the time they receive the gripping elements secured thereon to the time they comprise finished floss loop units and are ejected from the apparatus. Accordingly floss enters and exits each gripping unit along the same coaxial line as the floss lies in the gripping unit. Stated another way, the continuous strands of floss remain straight or parallel to each other throughout the entire process as opposed to being directed in transverse directions which would necessarily complicate and slow down the overall process and also result in gripping elements where the floss in the element lies at angles other than solely parallel as the floss was at the time manufacture took place.

After the floss loop units are formed on the continuous parallel strands of floss, such units are then automatically formed into dispenser packages by a variety of designs as follows. A plurality of continuous strands may be wound helically on a core whereby the gripping elements define a line parallel to the axis of the core; between these parallel lines is defined a cut line traversing floss between each two adjacent gripping elements of successive floss loop units. By a single cutting stroke along said cut line one can sever all the floss strands lying between individual floss loop units. Thereafter, one loop at a time can be removed from the core without disturbing or entangling the remaining loops wound helically. Alternatively, the continuous strands are wound spirally about a core building to a larger diameter. The outermost floss loop is unwound by pulling same and rotating the core, and one by one the outermost loops are severed from the remaining spiral wound floss units. A third alternative is to encase or encapsulate each floss unit separately from all the others by forming a heat sealed sleeve about these units. This is done by placing strips of transparent plastic above and below the continuous strands as they are discharged off the forming machine and heat sealing the outer edges of the strips forming a sandwich about the floss units and also heat sealing the ends between each floss unit. Subsequently when each unit is severed from the adjacent unit, it will automatically be completely sealed within its own package.

To make packaging more compact and efficient there are optional configurations for the gripping elements, for example, to have grooves parallel and adjacent the portions of floss traversing gripping elements, so that when such an element lies against floss strand of another floss unit in a spiral roll, the strand can fit within the grooves of the element of the other unit and therefore lie more compactly. This will also stabilize the spiral roll and reduce any tendency of same to unravel or tangle. With the helically wound loops about a core, it is useful to provide adhesive strips on the surface of the core against which the gripping elements stick to also help stabilize the overall package. In all of the above described embodiments of floss loop units, the gripping elements can be molded plastic pieces which can adhere very securely to dental floss, such pieces being made of nylon, ABS or other resin. Alternatively, the gripping elements can be a tape or other sheet material product or tabs with adhesive surface for adhering the two sheets together and very securely adhering the sheets to the floss at the places of engagement. The floss is typically nylon, rayon or other solid or braided material.

DESCRIPTION OF THE DRAWINGS

FIG. 1 is a top plan view of undivided floss loop devices along a continuous strand of floss from which they were made;

FIG. 2 is a single loop device severed from the succession of devices of FIG. 1;

FIG. 3 is a second embodiment of floss loop devices made from continuous strands of floss as a variation from the embodiment of FIG. 1;

FIG. 6a is a first embodiment of a packaging/dispenser for segments of floss loops;

FIG. 6b is a sectional view taken along line 6b—6b in FIG. 6a;

FIG. 7 represents another embodiment of the dispenser illustrated in FIG. 6A;

FIG. 8 is a second embodiment of a dispenser container with the floss loops wound spirally on a spool;

FIG. 9a is a front perspective view of another gripper element embodiment for a floss loop device;

FIG. 9b is a view similar to FIG. 9a of an alternate version of a gripper element;

FIG. 20b is a front elevation of an assembly of loop devices packaged in the dispenser of FIG. 20a;

FIG. 20c is a rear perspective view of the package of FIG. 20a;

FIG. 21a is a fragmentary front elevation view of another dispenser arrangement;

FIG. 21b is a side elevation thereof;

FIG. 22 is a fragmentary perspective view of another dispenser arrangement;

FIG. 23 is an exploded perspective view of another embodiment of loop gripping device and floss assembly procedure;

DETAIL DESCRIPTION OF THE PREFERRED EMBODIMENTS

Figure 4:
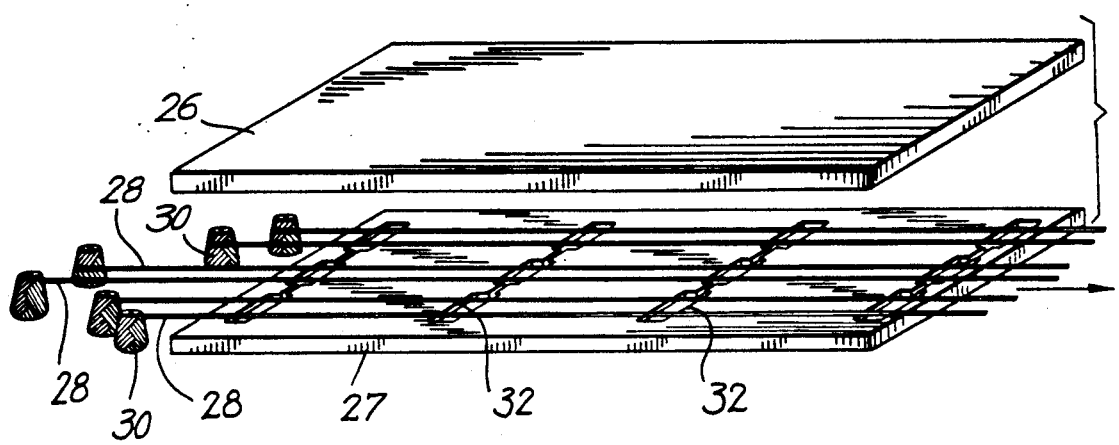
FIG. 4 is a schematic representation of an injection molding apparatus for forming gripping elements on continuous strands of floss.

FIG. 1 represents schematically the method of manufacturing floss loops where two strands of dental floss 10 and 12 from corresponding sources of floss (not shown) are directed to be parallel and closely adjacent, and at designated intervals gripping elements 18 are secured to the floss strands which remain parallel throughout. Each gripping element is formed with a score line or otherwise weakened area indicated by line 20, and at a later stage each element 18 is broken or cut along this score line at which time the parallel floss strands therein are also severed. The resulting product, a single floss loop 22, is shown in FIG. 2 where the gripping elements 18a each constitute half of the original element 18 cut along line 20. Element 18 and the line 20 are designed so that the resulting cut element 18a would have no sharp or rough edges, since that part would be held between the user's fingers and placed within the user's mouth.

FIG. 3 illustrates a different embodiment of the continuous floss loops as made in FIG. 1. In FIG. 3 each loop unit is made separately by forming pairs of gripping elements 24 at intervals of dimension "a". Subsequently, the floss is cut between the two elements of each pair and there is no requirement to cut or break each individual floss element into two parts as in FIGS. 1 and 2.

Where the embodiment of FIG. 1 or FIG. 3 is selected, the length of floss between a pair of gripping elements would typically be about three inches. In FIG. 3 the distance between the gripping elements 24 of two adjacent loops or loop is indicated by dimension "b" which would be up to one half inch. Dimension "c" indicates the length of a typical element 24 in the axial direction which in this case is approximately ⅛ of an inch. The length of element 24 extending in the direction perpendicular to the axis of the floss is about ¾ of an inch, and the thickness of each element is about 1/16 of an inch. These dimensions all may vary with design considerations, some of which will be discussed in greater detail below. It should be noted that the floss enters and exits each gripping element at entry and exit points 23 and 25 respectively, such that the floss strands within the element lie parallel to each other and coaxial with the strands between the elements when said strands are extended lengthwise.

Figure 5:
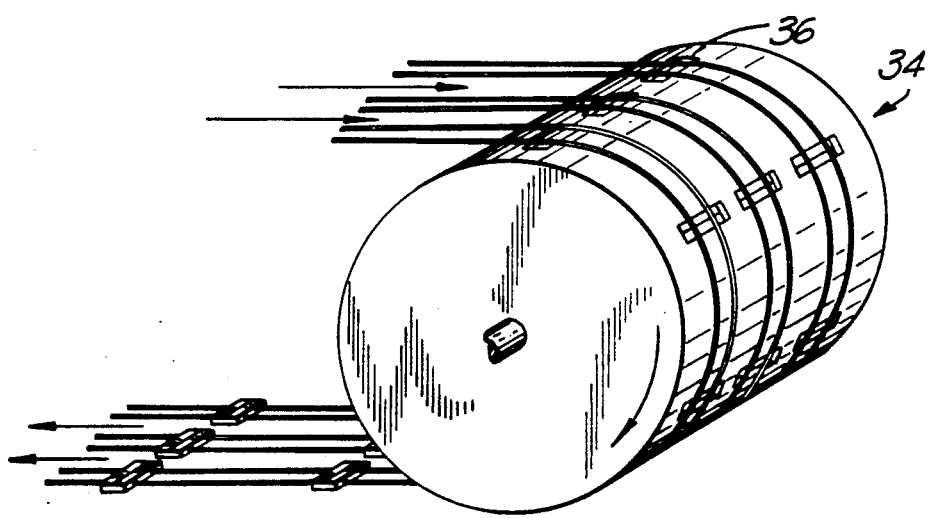
FIG. 5 is a schematic representation of a drum type injection molding apparatus as an alternate to that of FIG. 4.

FIG. 4 indicates schematically how the products of FIGS. 1 or 3 could be made with mold parts 26 and 27 operated in an injection molding machine (not shown) but which would be typical of prior art apparatus. As further indicated in this figure the continuous floss strands 28 are fed from a source of floss 30 to overlie cavities 32 where the gripping elements are formed. Appropriate ducts, not shown, for the injection molded plastic, typically nylon, to flow are provided. FIG. 5 schematically illustrates a rotary mold 34 with cavities 36 which operates continuously as contrasted with the intermittent type mold 26, 27 of FIG. 4 which must open at a predetermined cycle.

The process of making floss loops as described above reaches its highest efficiency only if the loop products are packaged on line at the time of their creation. The result would be individual loops in their own separate packages, or a plurality of loops in a single package maintained to avoid entanglement while in the package and while each is individually removed, regardless of whether they are cut apart before packaging or at the time of removal.

A first embodiment of a suitable dispenser package is shown in FIGS. 6a and 6b where a core or card 40 is provided about which the continuous strands of floss defining intermittent floss loops are helically wound from one end 42 to the opposite end 44. A typical loop 46 comprises two strands 48 and 50 and its two gripping elements 52 and 54 adjacent and on one surface 56 of core. For convenience the loops are aligned so that all the left hand gripping elements 52, 52', 52" etc. define a first line parallel to a second line formed by all the right hand elements 54, 54', 54" etc.

Prior to the helical winding of the loops, one or two strips of double-sided adhesive material 58 are placed along the top surface 56 of the core 40, such that the various gripping elements 52, 54 etc. adhere to this surface immediately as they are wound. The final step is to sever the dual strands of floss along a line 60 which extends transversely of this floss and parallel to the lines of gripping elements 52, 52', 52" etc. FIG. 6b illustrates a cross-section of the package shown in FIG. 6a with the gripping elements 52 and 54 adhering to two adhesive strips 58. Now the dispenser package is complete except for an optional sleeve or cover (not shown) which may be opaque or transparent to surround and protect the wound loops. Each loop can be easily removed by peeling the gripping elements off the adhesive strip without disturbing the remaining loops.

FIG. 7 shows an alternative embodiment which omits the adhesive strips 58 and substitutes therefor projections 62 out of the core 64 which engage an inner surface 64 in the bottom surface of each gripping element 66. A great many other means for engaging and securing the gripping elements onto the core are possible.

FIG. 8 shows a different version of a dispenser-container 68 for the above-described floss loops wherein a central spool 70 has the continuous floss strands of unsevered loops 71 wound spirally to define a core or roll rotatably mounted within housing 72. The floss loops are drawn off the roll by pulling the outermost end as one would do with a SCOTCH brand mending tape dispenser. In this particular case the outermost visible floss loop 74 defined by its gripping elements by the cutter 82. A flexible window 84 is formed by a pair of flexible leave 86 which allow the gripper elements to pass through in the direction of arrow 88, but restrain each gripper from returning back through the window. Thus in order to sever the floss at point 80 one must pull the visible loop 74 far enough until the first gripping element 90 of the next loop 92 has passed through the window. Thereafter element 90 will be easily accessible for pulling the loop 92 out of the dispenser to the point where it is ready to be severed from the remaining roll.

FIG. 9a illustrates a still different embodiment of the floss loop gripper element 94 which has portions eliminated to render this element lighter, less expensive, and more flexible. FIG. 9b illustrates a disc-shaped gripper element 96 as contrasted with rectangular elements of FIG. 3.

Figure 11:
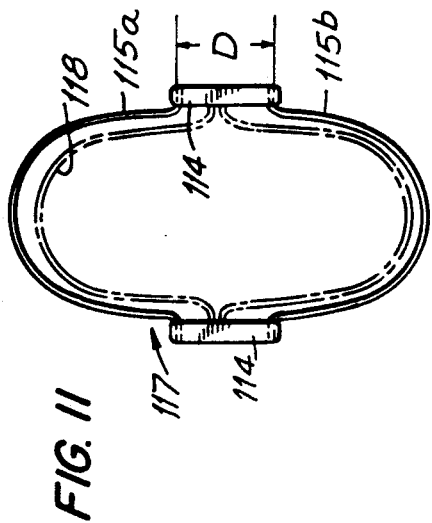
FIG. 11 is a single floss loop device taken from the succession of devices in FIG. 10.
Figure 10:
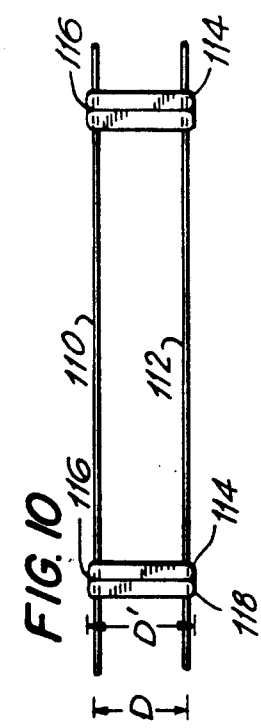
FIG. 10 is another embodiment of the unseparated floss loop devices shown in FIG. 1.

FIG. 10 shows a floss loop construction generally similar to that of FIG. 1, with a pair of continuous floss strands 110, 112 and a pair of gripping elements 114 each being severable along a transverse score line 116. The difference from FIG. 1 is that the floss strands 110 and 112 are placed very close to the outer edges 118 of the gripping elements so that the distance D between the floss strands is almost the same as the distance D' between the edges of the element. This will provide a floss loop product 117 as illustrated in FIG. 11 which is similar to that of FIG. 2 except for the feature described immediately above. With this feature in FIG. 11 gripper element 114 is generally aligned with the floss strand, between and contiguous with segments of floss 115a and 115b. When the user's finger is positioned adjacent element 114 in this embodiment where the floss is widely separated by dimension D, the element 114 will tend to remain in the aligned orientation shown rather than flop freely which would be the tendency if the floss strands were close together as indicated in dotted line 118 in FIG. 11.

Figure 13:
FIG. 13 is a cross section of a loop in its package taken along line 13—13 of FIG. 12.
Figure 12:
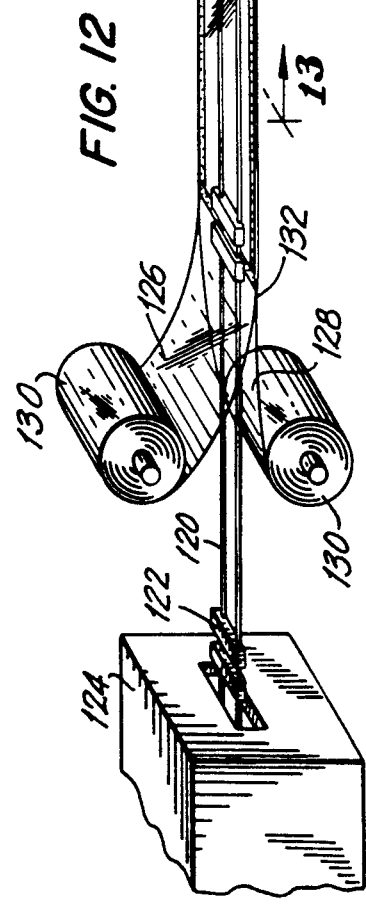
FIG. 12 is schematic illustration of a packaging assembly.
Figure 14:
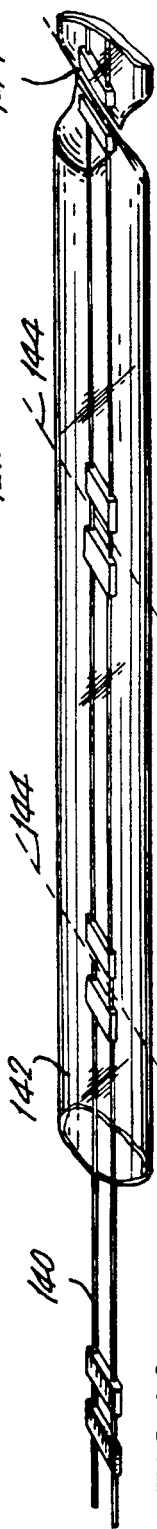
FIG. 14 is a fragmentary top perspective view of continuous floss loop devices partially within a plastic tubular envelope.

FIG. 12 illustrates a further embodiment for automatically packaging the floss loop products into a dispenser container. Continuous strands 120 with pairs of gripper elements 122 are discharged from the forming apparatus 124, and a transparent plastic sleeve or envelope 125 is formed by directing strips 126 and 128 of such plastic from source 130 to form a sandwich or laminate 132 above and below the successive floss loops. This laminate is heat sealed along dotted lines 134, 136 to define and seal each floss loop in an independent and separate package. At a subsequent time the continuous plastic sandwich can be severed along lines 138 between each individual floss loop segment. FIG. 13, illustrated in section, shows how the sandwich appears with the gripping element 122 between plastic layers 126 and 128 with the heat seal lines 134 shown joining the plastic sheets.

As an alternative to making the plastic sleeve shown in FIG. 12, one could direct the floss product 14 axially through a pre-existing plastic, tubular envelope 142, then heat seal at intervals 144 to seal the units individually, followed eventually by severing or otherwise separating the units one-at-a-time, or heat sealing and severing simultaneously.

Figure 15:
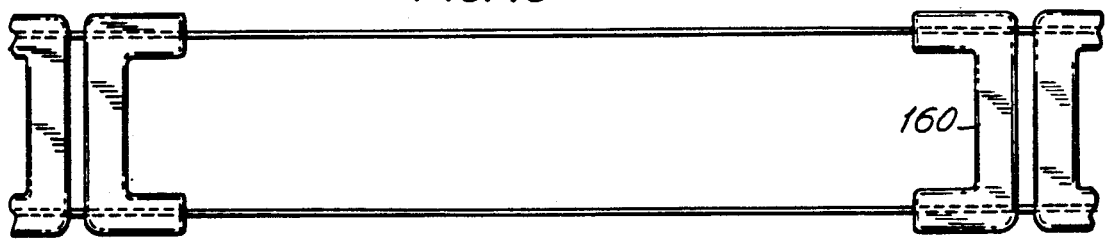
FIGS. 15 and 16 are top plan views of additional embodiments of floss loop devices.
Figure 16:
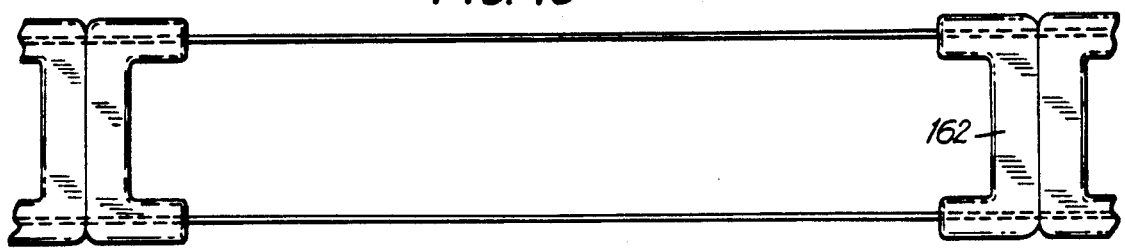
Figure 17B:
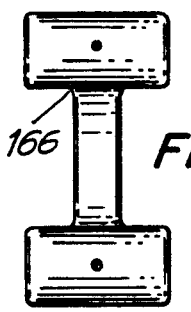
FIGS. 17b and 18b are corresponding end elevation views thereof.
Figure 17A:
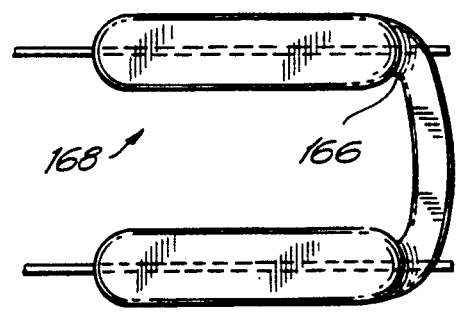
FIGS. 17a and 18a are plan views of other gripping elements.
Figure 18B:
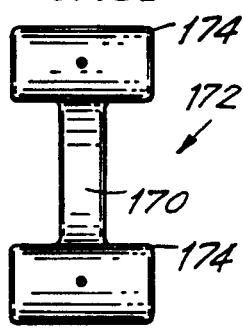
Figure 18A:
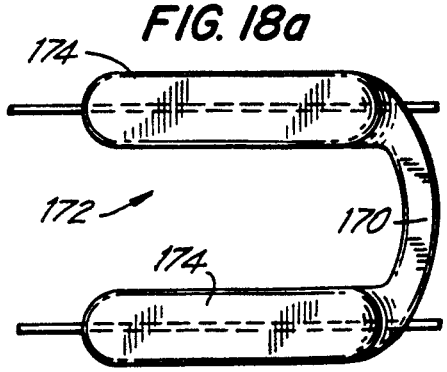

FIGS. 15 and 16 illustrate two additional embodiments of flosser units with gripper elements 160 and 162 corresponding generally to those of FIGS. 3 and 1 respectively. Gripper elements 162 in FIG. 19 break into two parts like those of FIGS. 1 and 10. These elements 160 and 162 are flexible so that when a loop is formed, as seen in FIG. 11, the gripper elements easily flex open to provide a more comfortable receptacle for a user's finger. To further assure easy flexing of the gripper element, the corners 166 of the element 168 in FIGS. 17a, 17b are narrowed or otherwise configured. FIGS. 18a, 18b show a variation of the gripping element of FIG. 17a, wherein high flexibility is provided by making the base 170 of the U-shape element 172 substantially thinner than the legs 174.

In connection with many of the embodiments of flosser units described above, each having a pair of floss segments extending between gripper elements, one can optionally select floss segments having different characteristics or flavors or both. Such characteristics may include thickness or diameter of flat, round or braided cross-sections, wax coating, nylon or other composition, and various flavorants and/or anti-plaque substances.

Figure 19A:
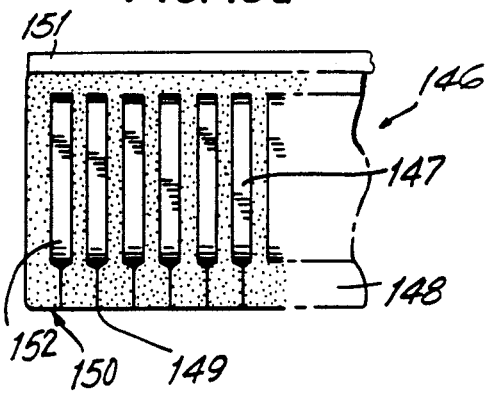
FIG. 19a is a fragmentary top plan view of dental loop devices in a dispenser package.
Figure 19B:
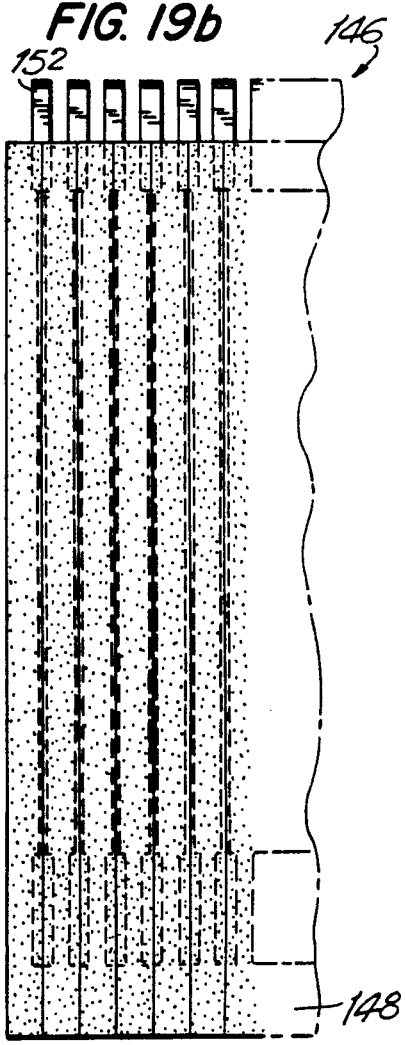
FIG. 19b is a fragmentary front elevation view thereof.
Figure 19C:
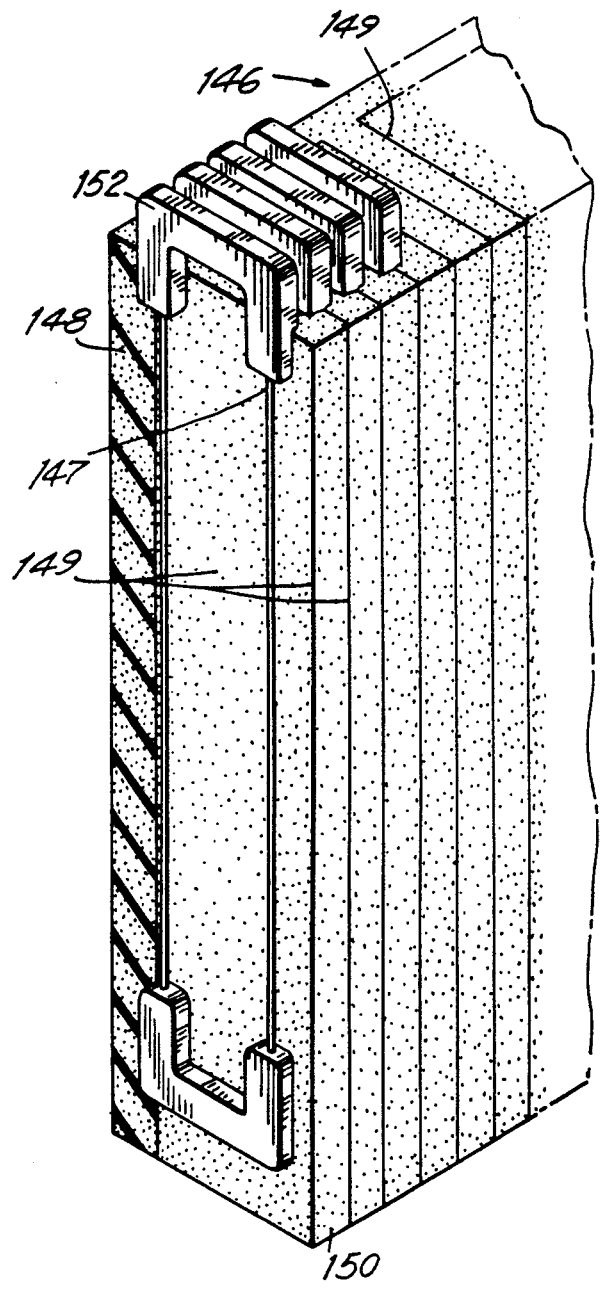
FIG. 19c is a fragmentary perspective view thereof.

FIGS. 19a-19c illustrate one embodiment of dispenser package 146 which maintains the loop devices 147 extended and untangled, while allowing easy removal of same. A block of resilient foam 148 has slits 149 extending parallel to each other and to the floss orientation, and extending rearward from the front surfaces 150 of the block. Optionally, a panel 151 may be attached to the rear surface of the block. Individual loop devices are positioned in each slit where they remain securely positioned by the pressure of the slit walls against the sides of the gripping elements 152. The upper elements are exposed to be grasped and pulled by a user who can easily extract the entire loop device. For insertion of these devices in the slits, the block may be first fanned open or the devices may simply be forced in. Afterward, a loaded block can be protected in any suitable housing, carton, blister pack or other container.

FIGS. 20a through 22 illustrate other arrangements for manufacturing, holding and dispensing the dental floss loop devices. In FIG. 20b there is an assembly 176 of devices whereby a plurality of individual devices 178 are injection molded together in molding apparatus not shown. The gripper elements 180 are joined to each other by plastic connectors 182 forming transverse arches 184, 186. The two arches are maintained apart by one or two support rods 188 which thereby maintain the strands of floss 190 extended linearly and not tangled with each other.

Figure 20A:
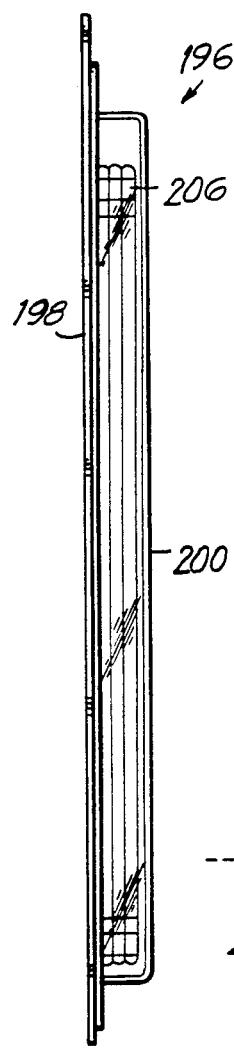
FIG. 20a is a side elevation of another dispenser package.
Figure 20D:
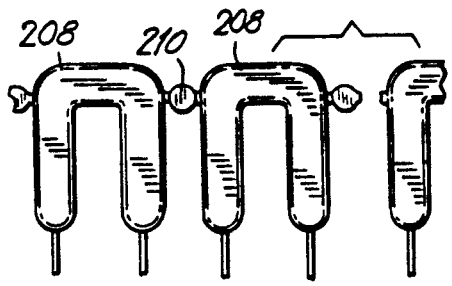
FIG. 20d is an enlarged fragmentary view of FIG. 20b.
Figure 20C:
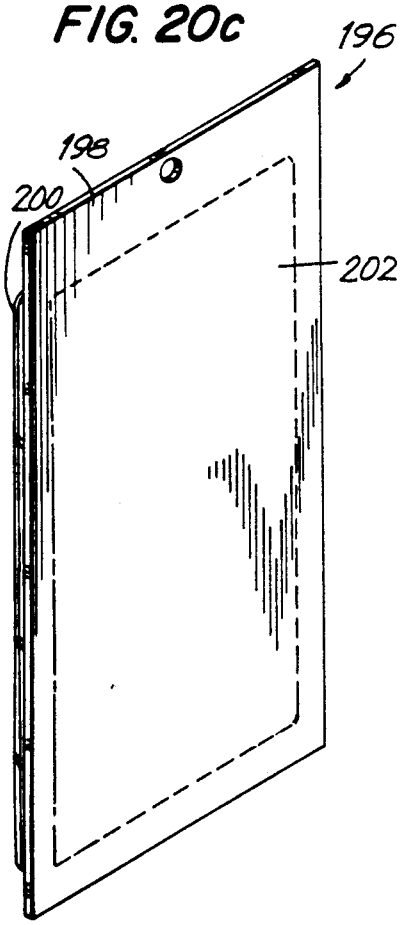
Figure 20B:
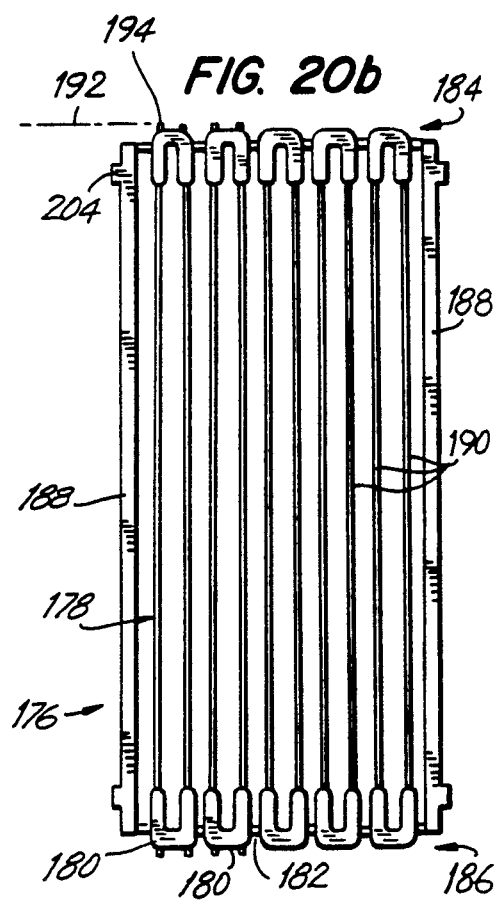

In manufacture of the assemblies shown in FIG. 20b, numerous similar assemblies can be positioned axially and made simultaneously, these assemblies being cut apart along transverse line 192 whereby the floss strands represented by 194 are also cut. The assembly or rack of FIG. 20b may be conveniently housed in a blister package 196 shown in FIGS. 20a and 20c, where a panel 198 receives a cover 200 heat sealed thereto. A flap 202 is bendable out of the plane of the panel to expose one of the plurality of racks positioned therein. Individual loop devices are then broken off the rack by bending first one gripper element at a junction point 182 and then bending the mate of the pair for each device. The remaining joined devices will remain intact until each is broken away.

The rack is further stabilized in the blister pack by its tab projection 204 which resides in and is guided by groove 206 in the cover 200.

FIG. 20d shows another embodiment of junction joining gripping elements where the elements 208 have junction element 210 which has reduced cross-sectional area at its end parts adjacent the gripping elements. When one gripping element is bent relative to the one adjacent, the break will occur at the smallest area, thus leaving a smaller projection on the gripping element.

FIGS. 21a and 21b show a simple arrangement whereby gripping elements 212 of loop devices 214 are engaged about pegs 216 on a panel 217 with a slight amount of tension in the floss 218. Individual loop devices are removed as desired; the arrangement can be housed in any desired container, blister package, etc. FIG. 22 shows a variation whereby floss units 220 are secured on panel 222 from which they are easily removable.

FIG. 23 illustrates a still further embodiment of gripping element 224 which has a slit or groove 226 for receiving the floss, where the floss is subsequently affixed by ultrasonic welding, clinching, gluing, or other chemical, mechanical or heat techniques.

The various U-shape gripping elements shown herein obviously are substantially flexible so that they will easily bend open and conform to the shape of a user's finger.

Typically the gripping elements and the floss are made of nylon, however, many other materials may be selected as long as the floss and gripper remain securely attached. Various manufacturing processes are possible among those already known in the prior art and as discussed in U.S. Pat. Nos. 4,016,892, 4,006,750, 2,180,522, and 2,187,899.

Figure 24:
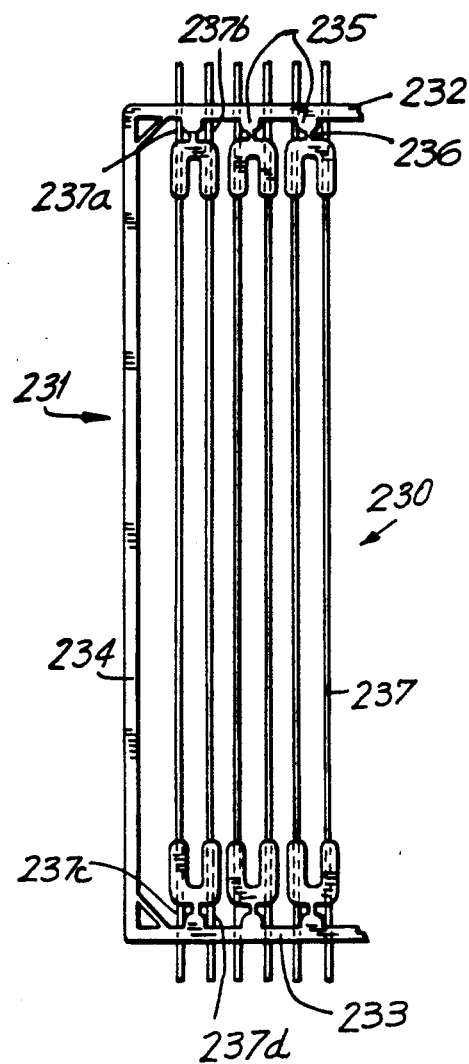
FIG. 24 is a front elevation view similar to FIG. 20b of another embodiment.
Figure 25:
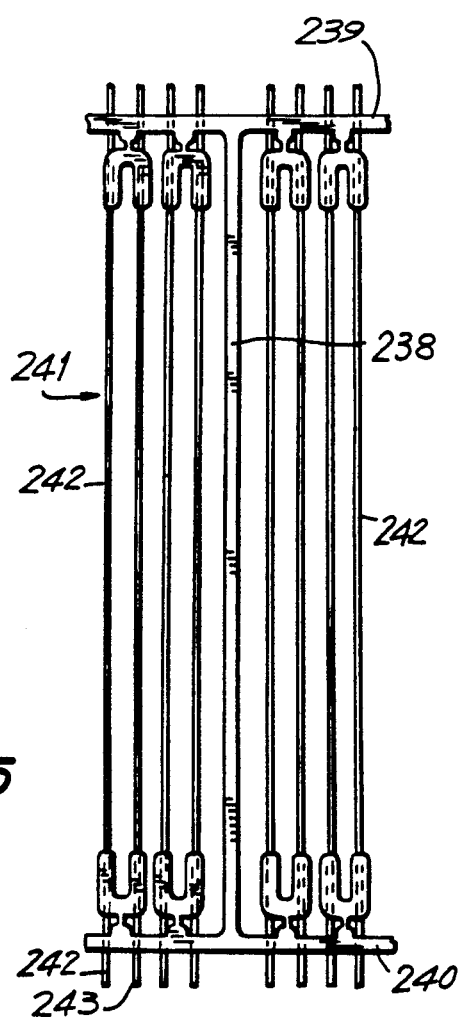
FIG. 25 is a front elevation similar to FIG. 24 of a further embodiment.
Figure 26:
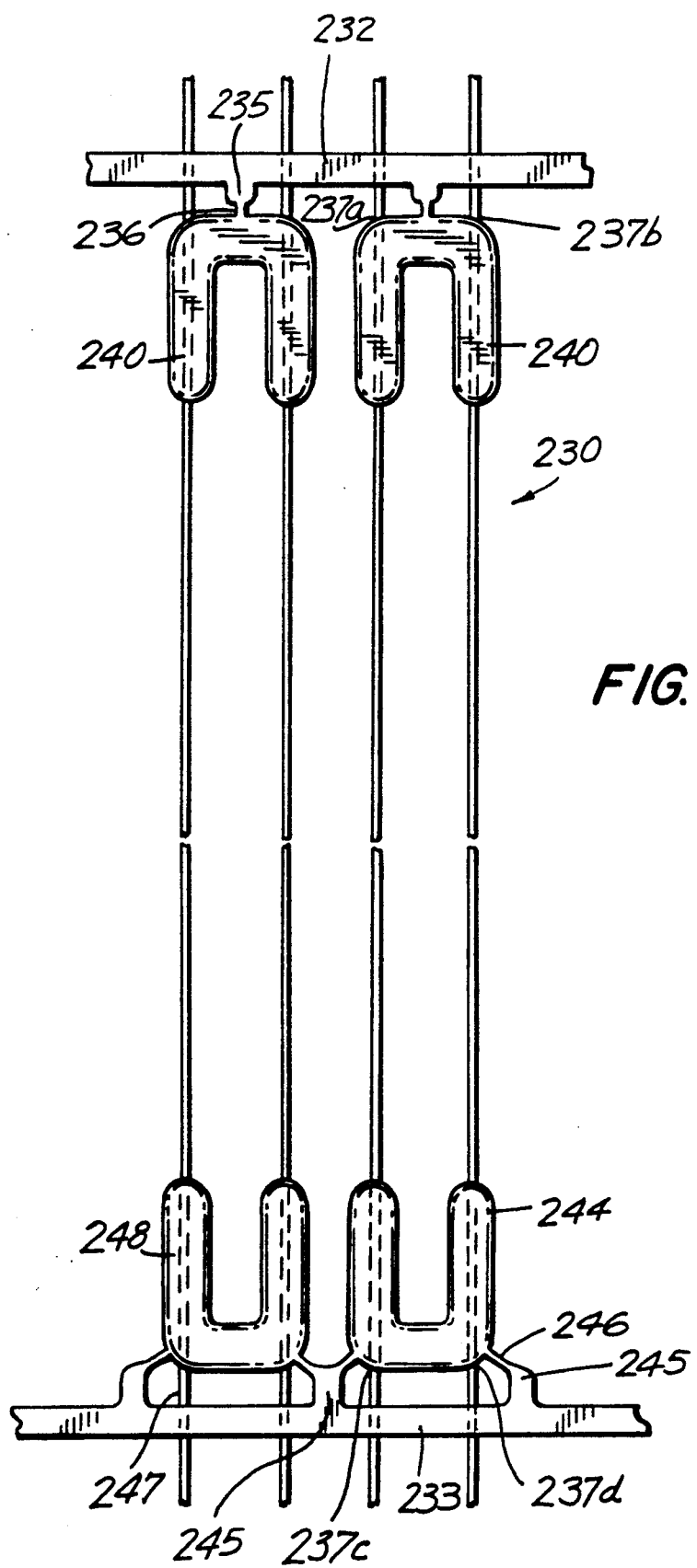
FIG. 26 is a fragmentary elevation similar to FIG. 24 of still further embodiments.

FIGS. 24-26 illustrate variations of the molding array shown in FIG. 20b. FIG. 24 shows a representative arrangement whereby gripping units 230 are molded simultaneously with a generally rectangular frame 231 formed by upper and lower beams 232 and 233 respectively and at least one vertical beam 234. Grippers 230 are each molded via a runner or feeder 235, each having a narrow neck 236 which readily breaks when a unit is separated from the frame.

Prior to packaging these arrays, each comprising a frame plus gripping units, the floss is cut at points 237a, 237b, 237c and 237d for each unit. Thus, a unit is held and supported in place by the breakable molded connectors 235.

Despite removal of one unit 230 at a time from the frame, the upper and lower beams 232, 233 thereof remain stiff enough to hold and stabilize the remaining units in their extended orientation shown, thus preventing tangling of the floss strands 237.

FIG. 25 shows another variation of the mold array where the frame's vertical support means comprises a single central beam 238 stabilizing upper and lower beams 239 and 240 respectively, which support the plurality of gripping units 241 whose floss strands 242, 243, etc. extend through the beams as shown. Some of the units are not shown but represented symbolically by parallel lines 241a. The total number of units in any molded array can vary as desired. The upper part of FIG. 26 shows greater detail of the array of FIG. 24, particular the narrow neck 236 which is readily breakable when a gripping element 240 is bent from the frame to remove a unit 230. As discussed earlier, the floss strands are cut at 237a and 237b, typically, very close to the gripper element 240 to provide a relatively clean and smooth surface.

The lower part of FIG. 26 shows a variation of the molded array of upper part of FIG. 26 where gripper 244, when molded, is fed or gated by runners or ducts 245 with narrow necks 246 extending from the lower beam 233. As before, the floss would be cut at 237c and 237d prior to packaging. In some instances plastic will flow, for example in FIG. 26, from beam 233 along the segment 247 of floss to the gripper element, forming a thin coating on the segment. This could occur because of the space allowed in the mold for the floss to lie when the mold parts are closed. Regardless of the result, the floss will be cut along said segment before packaging or by other means not shown when the unit is removed from a package. The various arrays of molded gripper units are all modifiable to fit into selected packages, blister packs, or other containers that may be selected.

It is understood that the dental floss loop devices, the methods of manufacturing same, and the methods and dispenser packages disclosed herein may include many variations in shape, composition and technique within the scope and spirit of the claims appended hereto.

I claim:

1. A dental floss loop device comprising a pair of injection molded plastic gripping elements and a pair of separate dental floss strands extending between said pair of elements with opposite ends of each floss strand secured respectively in the two elements of said pair, the two strands of said pair are equal in length and the two gripping elements of each pair are generally similar, the two ends of floss within each elements defining along their entire length within the element a pair of generally parallel lines, each gripping element is generally U-shaped with said floss strands extending axially through the legs of the U, and the base of the U extending transversely of said floss.

2. An assembly of dental floss devices, where each device comprises a pair of spaced-apart first and second injection molded plastic gripping elements and a pair of dental floss segments extending between said pair of elements, with opposite ends of each floss segment secured respectively to the two elements of each pair, said assembly comprising a plurality of said devices situated in spaced parallel relationship, the floss strands of each device extending axially in a generally straight line, each of said first gripping elements being contiguous with and joined to other first gripping elements immediately adjacent thereto, each of said second griping elements being contiguous with and joined to other second gripping elements immediately adjacent thereto, said assembly further comprising at least one generally stiff first support means extending between and having its ends respectively joined to one pair of said first and second gripping elements, whereby said first support means maintains said first elements spaced apart from said second elements of each pair respectively and maintains said strand between each pair of first and second elements generally straight, each device being separable from an adjacent device by breaking off one pair of first and second elements relative to the adjacent pair of first and second elements to which they are joined.

3. An assembly according to claim 2 wherein said first support means comprises a rod oriented generally parallel to said strands and said parallel strands define a succession of parallel lines from first to last, and said support means is situated approximately midway between said first and last strands.

4. An assembly according to claim 2 wherein said first support means comprises a rod oriented generally parallel to said strands and said parallel strands define a succession of parallel lines from first to last, and said support means is situated outward and adjacent said first strand.

5. An assembly according to claim 2 further comprising junction means joining each two mutually adjacent first gripping elements and each two mutually adjacent second gripping elements.

6. An assembly according to claim 5 wherein said first and second gripping elements are injection molded plastic and each of said junction means comprises injection molded plastic the same as and contiguous with said gripping elements.

7. An assembly according to claim 6 wherein each of said junctions has a central part and has end parts immediately adjacent a gripping element, said end parts having cross-sectional area substantially less than that of said central part, whereby, when said junction is bent, an end part will break more readily than said central part.

8. A dental floss loop device comprising a pair of injection molded plastic gripping elements, each being flexible and bendable to a generally convex shape when pressed by a user's finger, and a pair of separate dental floss strands extending between said pair of elements with opposite ends of each floss strand secured respectively in the two elements of said pair, the two strands of said pair are equal in length and the two gripping elements of each pair are generally similar, the two ends of floss within each elements defining along their entire length within the element a pair of generally parallel lines.

9. A device according to claim 8 wherein said base of the U is smaller in cross-section and more flexible than said legs in cross-section.

10. A dental floss loop device comprising a pair of injection molded plastic gripping elements and a pair of separate dental floss strands extending between said pair of elements with opposite ends of each floss strand secured respectively in the two elements of said pair, the two ends of floss within each elements defining along their entire length within the element a pair of generally parallel lines, an assembly of loop devices wherein said devices are situated in succession with one gripping element of each device being adjacent one gripping element of the next successive device, wherein the pairs of floss strands of each device are contiguous between and joining each two adjacent devices, each device being separable from the adjacent device when the floss strands therebetween are severed and wherein adjacent gripping elements of each two successive devices are joined and contiguous and are separable from each other by forcible separation.

* * * * *